US011284930B2

(12) United States Patent
Formica et al.

(10) Patent No.: US 11,284,930 B2
(45) Date of Patent: Mar. 29, 2022

(54) FOCUSED TREATMENT TIP DESIGN AND METHOD TO OPTIMIZE HEAT TRANSFER THROUGH LOW TEMPERATURE FLUIDS AND GASES

(71) Applicant: CRYOCONCEPTS LP, Bethlehem, PA (US)

(72) Inventors: Philip Michael Formica, Bethlehem, PA (US); Lincoln C. Young, Bethlehem, PA (US); Amanda Devine, Bethlehem, PA (US); R. Sam Niedbala, Bethlehem, PA (US)

(73) Assignee: CRYOCONCEPTS LP, Bethlehem, PA (US)

( * ) Notice: Subject to any disclaimer, the term of this patent is extended or adjusted under 35 U.S.C. 154(b) by 0 days.

(21) Appl. No.: 16/857,642

(22) Filed: Apr. 24, 2020

(65) Prior Publication Data
US 2020/0337755 A1 Oct. 29, 2020

Related U.S. Application Data

(60) Provisional application No. 62/839,156, filed on Apr. 26, 2019.

(51) Int. Cl.
*A61B 18/02* (2006.01)
*A61B 18/00* (2006.01)

(52) U.S. Cl.
CPC ............ *A61B 18/0218* (2013.01); *A61B 2018/00101* (2013.01); *A61B 2018/0256* (2013.01)

(58) Field of Classification Search
CPC ...... A61B 18/0218; A61B 2018/00101; A61B 2018/0256
See application file for complete search history.

(56) References Cited

U.S. PATENT DOCUMENTS 5,200,170 A * 4/1993 McDow ............ A61B 18/0218
128/DIG. 27
8,672,931 B2 * 3/2014 Goldboss ............ B65D 83/303
606/22

(Continued)

FOREIGN PATENT DOCUMENTS

WO 2007/028975 A1 3/2007

OTHER PUBLICATIONS

International Search Report and Written Opinion of PCT International Application No. PCT/US2020/029764, dated Jul. 15, 2020.

*Primary Examiner* — Daniel W Fowler
(74) *Attorney, Agent, or Firm* — J.A. Lindeman & Co. PLLC

(57) ABSTRACT

A focused treatment tip (FTT) for controlling the evaporation rate and providing targeted delivery of low temperature liquified gases for contact with living tissue includes a contoured body. When filled with liquified gas, the device insulates the gas from waste heat sources, such as the surrounding environment. The device can control the evaporation rate of the liquified gas at the treatment site. The controlled evaporation rate affects the rate of heat transfer from the treated tissue allowing for controlled exposure times and desired outcomes. The device can be used with various application tips to further define the target tissue area to be treated while minimizing collateral damage to surrounding tissue and isolating the gas within the contoured body and focusing heat transfer to the desired treatment area. The device may use transparent materials that make the treatment visible to the operator while the liquified gas is evaporating.

16 Claims, 7 Drawing Sheets

(56) References Cited

U.S. PATENT DOCUMENTS

| | | | |
|---|---|---|---|
| 2007/0005048 A1* | 1/2007 | Niedbala | A61M 35/003 606/22 |
| 2008/0221561 A1 | 9/2008 | Geiger | |
| 2008/0306474 A1 | 12/2008 | Steinfatt | |
| 2009/0209952 A1* | 8/2009 | Van Der Heijden | A61B 18/0218 606/22 |
| 2015/0313662 A1 | 11/2015 | Ottanelli | |
| 2018/0140344 A1 | 5/2018 | Rossel | |

* cited by examiner

101

FOCUSED TREATMENT TIP DESIGN AND METHOD TO OPTIMIZE HEAT TRANSFER THROUGH LOW TEMPERATURE FLUIDS AND GASES

CROSS-REFERENCE TO RELATED APPLICATION

This application claims the benefit of priority of U.S. Provisional Application No. 62/839,156 filed on Apr. 26, 2019. This application incorporates by reference the entire contents of U.S. Provisional Application No. 62/839,156 filed on Apr. 26, 2019.

TECHNICAL FIELD

The invention relates to cryosurgical devices and methods of treating tissues to remove unwanted topical lesions. In particular, the invention relates to devices and methods to isolate applied liquified gases, focusing their potential heat transfer on the target tissue, and controlling heat lost to secondary sources, such as the surrounding environment. The geometric construction of the devices provides freezing and controls the rate of evaporation and, therefore, the rate of heat transfer at the interface between the gas and target tissue.

BACKGROUND

The treatment of cutaneous lesions on humans and animals is often accomplished by dispensing liquified gases into a cone or funnel. In cutaneous cryosurgeries, the liquified gas contacts the treatment surface, draws heat from the contact point with the tissue, and freezes the tissue by overcoming the local tissue temperature when the liquified gas is allowed to stay in contact long enough or when sufficient liquified gas is applied. The cells in the frozen tissue are damaged and are eventually sloughed off by the body resulting in new cell growth.

Existing cryosurgical devices and methods use a simple cone or funnel design to direct the liquified gas to the target spot (treatment area). This results in rapid evaporation due to the liquified gas drawing heat not only from the target contact spot, but also from the surrounding environment and cone materials. This results in an inconsistent treatment and an overall decrease in efficacy as reflected by the need for more gas to achieve the desired result. Existing cone or funnel designs have a large open end, maximizing the area for heat loss to the environment instead of concentrating it towards the treatment area. The inefficiency of current designs results in increased treatment times and increased volumes of liquified gas applied to the target spot being treated.

SUMMARY

The methods and devices of the invention include focused treatment tips (FTT) and overcome the inefficiency of previous designs by controlling heat transfer from the surrounding environment. The materials selected for the FTTs provide enhanced focus on the target spot being treated and provide further improvements and benefits over prior systems. The invention includes improved constructions of the interface at the surface of the skin and the head space above the gas. The invention provides an improved gas dispenser interface. The invention provides improved methods of controlling the rate of evaporation and enhances heat transfer at the surface of the skin and target treatment spot. The invention provides a more effective cryosurgical treatment of lesions while using less liquified gas to achieve the result.

The invention can be used with other apparatus and/or methods that dispense liquified gases. The invention includes a focused treatment tip (FTT) that provides a targeted heat transfer from treatment surfaces and from target tissues when placed into contact and supplied with liquified gas. The FTT can be fit with interchangeable application tips that allow treatment of lesions of varying shapes and sizes. The FTT can be clear or opaque and can be composed of polymers, elastomers, metals, silica, and combinations of these materials. In one example embodiment of the invention, translucent materials are used to allow the observation of the liquified gas "boiling," while dwelling at the FTT interface with the treatment spot. The improved visual observation allows an operator to monitor the treatment over time.

The invention allows the operator to control the time that the liquified gas is in contact with the target skin through evaporation and the amount of heat transferred during the gas contact period. To control this timing and delivery, FTTs in accordance with the invention include features that influence the rate of evaporation and provide control against random heat acting as the primarily cause of evaporation of the liquified gas. FTTs in accordance with the invention are designed and manufactured to provide these controls based on geometric and material selections of the sections of the FTTs where they contact the treatment area (i.e., interface at the skin), in the boiling section, and in the evaporation control section.

The interface section of the FTTs at the skin cover the target treatment area while minimizing the volume of liquified gas needed to cover the target skin. To provide these features, the interface tip section is shaped to match the geometry of the skin being treated.

In some example embodiments of the invention, the FTT includes an application treatment tip with various geometries (e.g., diameters) and depths to allow targeted treatments to match lesion sizes. The application tips can be made of various materials and may be reused after appropriate sterilization or discarded. The application tips can be of various shapes for the surface interface and skin contact, (e.g., ovals, squares, rounded squares, diamonds, rounded diamonds, triangles, rounded triangles, and other geometrical shapes with or without rounded corners and/or edges). The method of making the seal between the FTT and the skin may be through mechanical pressure, adhesives, or multilayered laminates.

The boiling section is in fluid communication with the skin interface section and is adjacent to the skin interface section and is designed and manufactured to allow the liquified gas to evaporate within a confined space, thus limiting the exposed surface area of the liquified gas to the environment surrounding the device. The portion of the boiling area opposite the skin interface section is in fluid communication and adjacent to the evaporation control section. The boiling section dimensions can be adjusted on each end (the end adjacent to the skin interface section and the end adjacent to the evaporation control section) to speed or slow the evaporation rate of the liquified gas.

The evaporation control section is the main interface between the open environment and the gas. Vapor transfer takes place in this section, and the amount of surface area and the unobstructed opening size of the evaporation control section serves to control the rates of evaporation. The sizes and geometries of the evaporation control section can be modified to control the rates of evaporation. In tandem with the interface section of the FTT, as the size of the interface section increases, so does the heat loss, which increases the rate of evaporation.

The combination of the skin interface section, the boiling section, and the evaporation section combine in the FTTs in accordance with the invention to control the rate of evaporation for cryogen gases used for cryosurgical treatments.

In one example embodiment of the invention, a focused treatment tip (FTT) device interfaces with a cryosurgical device and provides evaporation rate control of liquified gases in contact with a patient. The focused treatment tips (FTTs) include an evaporation control section that receives the cryosurgical device, a boiling section that is in fluid communication with the evaporation control section also in fluid communication with an application tip section. That is, the boiling section is between the evaporation control section and the application tip section. The boiling sections include a determined space for vapor transfer of the liquified gas when treating a targeted tissue treatment site of the patient. The application tips ("skin interface") cover the targeted tissue treatment site of the patient and seal the FTT device to the tissue treatment site of the patient.

In one example embodiment of the invention, an FTT device includes a clear or opaque material, enabling a user or operator to observe boiling of the liquified gas during the treatments. The materials can include polymers, elastomers, metals, silica, and combinations of these materials.

In example embodiments of the invention, the FTT devices include a contoured elongated body for one-handed operation. Prior commercial products with cones required a two-handed operation with one hand holding the cone in contact with the skin at the target lesion while simultaneously using a second hand to dispense gas into the cone, allowing it to evaporate. Prior systems suffered from rapid evaporation caused by heat from waste sources, such as the local environment and surroundings and must be filled several times to treat the target area for a sufficient amount of time for the desired treatment effect.

As well, the volume of the boiling section is proportional to the evaporation rate of the liquified gas. The geometric dimensions of the boiling section can be selected and manufactured to provide a target evaporation rate or range of evaporation rates of the liquified gas.

The liquified gases used in accordance with the invention include hydrocarbons, fluorocarbons, hydrofluoro-olefins, and hydrofluorocarbon blends. Likewise, the liquefied gases used include propane, butane, dimethylether, 1,1,1,-trifluoroethane, pentafluoroethane, difluoromethanene, trifluoromethane, chlorodifluoromethane, 1,3,3,3-Tetrafluoropropene, and nitrous oxide.

The application tip section of the FTTs in accordance with the invention are sized and shaped to approximate the size and shape of the targeted tissue treatment site. For example, the application tip section of the FTTs can be ovals, squares, rounded squares, diamonds, rounded diamonds, triangles, rounded triangles, and other geometric shapes.

One example embodiment of the invention includes a cryosurgical device, including a liquified gas delivery device and a focused treatment tip (FTT) device as outlined above. Another example embodiment of the invention includes a method for treating a skin lesion using a cryosurgical device with a focused treatment tip (FTT) device. One method includes positioning the FTT device against a targeted tissue treatment site or over a skin area to be treated. The example method in accordance with the invention includes receiving liquified gas into the FTT device to a determined fill level and maintaining the FTT device against the targeted tissue treatment site while the liquified gas is evaporating. As the liquified gas evaporates, the liquified gas draws heat from the skin/tissue treatment site. Once the liquified gas evaporates, the FTT is removed from the treatment area. In one example embodiment, the method of treating the skin lesion can be repeated when an additional application is indicated. The cells at the treated spot are now damaged or destroyed, and the body will slough off the damaged cells in approximately two weeks.

DETAILED DESCRIPTION

The FTT (focused treatment tip) devices of the invention deliver cryosurgical substances to affected patient areas for treatments.

System Components

Figure 1:
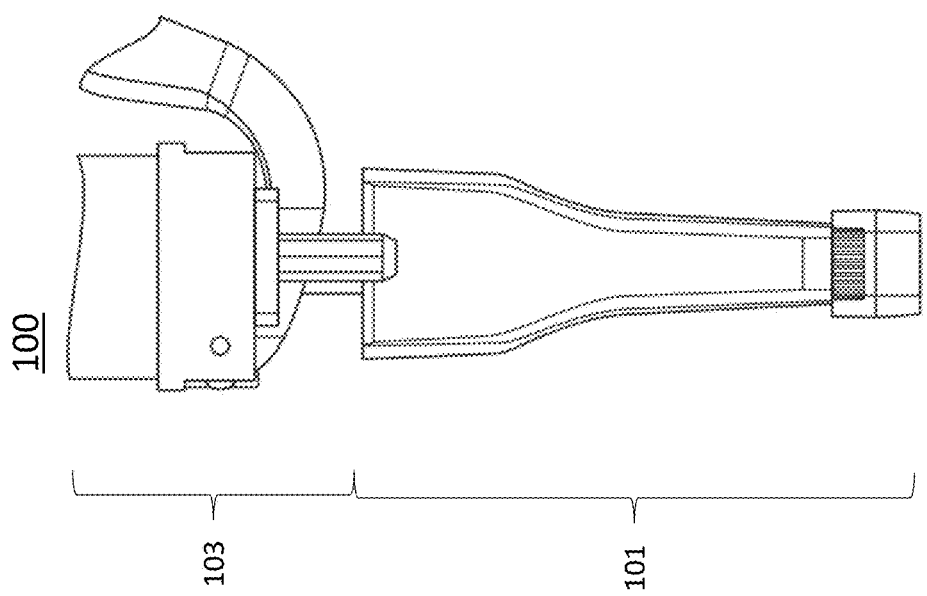
FIG. 1 shows a perspective view of a cryosurgical device including an FTT (focused treatment tip) device for cryosurgical applications in accordance with the invention.

As shown in FIG. 1, a cryosurgical system 100 includes an FTT device 101 configured to mate with a cryosurgical device 103 for cryosurgical treatments. The cryosurgical substance delivery device 103 can be any number of liquified gas delivery devices for targeting affected skin. The cryosurgical device 103 may include a storage container for liquified gas and a dispersal mechanism to dispense the stored liquified gas for cryosurgical treatment. The cryosurgical device 103 may also dispense various cryogens for use with the FTT device 101.

The FTT devices 101 may include many shapes and sizes to be adapted to treatment sizes and shapes of treatment locations. The FTT devices 101 may include a contoured elongated body to provide space for evaporation of the liquified gas for an effective time of delivery. The FTT devices 101 of the invention can include clear or opaque material compositions to allow for user observation of the cryosurgical substances as it boils/bubbles and evaporates once the cryosurgical substance is dispensed. Additionally, the FTT devices 101 are configured to mate with the cryosurgical device 103 to provide single-handed control of the cryosurgical system during treatment. The FTT devices 101 limit the effects of environmental evaporation and seal the delivery of the liquified gas to the affected skin to provide more effective cryosurgical treatment.

Figure 2:
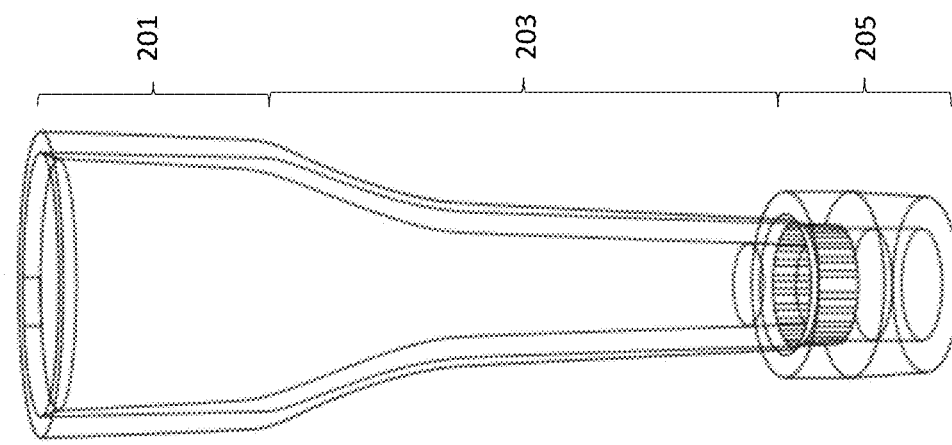
FIG. 2 shows a perspective view of an FTT device for cryosurgical applications in accordance with the invention.
Figure 3:
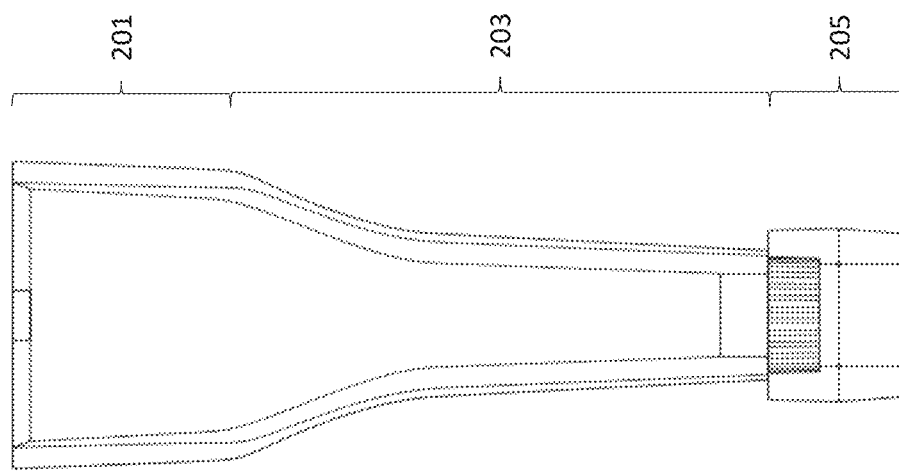
FIG. 3 shows a side view of an FTT device for cryosurgical applications in accordance with the invention.
Figure 4:
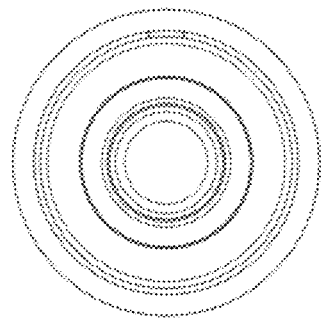
FIG. 4 shows a top view of an FTT device for cryosurgical applications in accordance with the invention.

As shown in FIGS. 2-4, the FTT devices 101 include at least three designed sections: (1) an evaporation control section 201; (2) a boiling section 203; and (3) an application tip skin interface 205. The FTT devices 101 may be unibody devices, or multi-bodied interfacing devices which have interchangeable evaporation control sections 201, boiling sections 203, and application tip to skin interfaces 205 to configure to the geometry of the affected skin, the mating portion of the cryosurgical device 103, and for providing space for vaporization of the cryogen gas. The sections 201-205 of the FTT devices 101 control the rate of evaporation by defining the geometry of each section of the FTT. The sections may be optimally configured and manufactured based on the type of liquified gas used for treatments and the boiling temperatures of those liquified gases being used. Similarly, the sections can be configured based on the size and shape of the affected skin or anatomical region undergoing treatment.

The evaporation control section 201 initially receive a liquified gas from a cryosurgical device 103. The evaporation control section 201 is the main interface between the open and uncontrolled environment and the liquified gas, and thus greatly controls evaporation of the liquified gas. Vaporization takes place within the cross-sectional area of the evaporation control section 201 interfacing to the cryosurgical device 103. For example, the cross-sectional area of the evaporation control section 201 and the volume of space within the evaporation control section 201 (i.e., the cross-sectional area in combination with the length) controls the rates of evaporation.

The boiling section 203 is between the evaporation control section 201 and the application tip skin interface 205. The boiling section 203 is configured and manufactured to allow the gas to evaporate within a confined volume, thus limiting the environmental thermal effects on the liquified gas to control vaporization prior to treatment. The boiling section 203 dimensions may be adjusted on each end (i.e., at the end that interfaces with the evaporation control section 201 and at the end that interfaces with the application tip skin interface 205) in order to speed or slow evaporation. For example, the boiling section 203 may be increased in length, width, or cross-sectional area to increase the surface area of the liquified gas to allow proportionally faster evaporation of the liquified gas.

The configurations of the cross-sectional areas of the evaporation control section 201 and boiling section 203 may be shaped in various ways, but as the size of the interface with the cryosurgical device 103 increases with the environment, so will the heat losses, thus increasing the gas evaporation. Thus, the evaporation control section 201 and boiling section 203 are configured and manufactured to more effectively maintain the temperature of the liquified gas by controlling the surface area of the connection to the cryosurgical device 103 thereby controlling the rate of evaporation of the liquified gas. The evaporation control section 201 and boiling section 203 may be configured and manufactured to mate with various cryosurgical devices 103 to provide single-handed use of the cryosurgical system 100. Thus, the dimensions of such a mating interface with the evaporation control section 201 and boiling section 203 may determine the length of the evaporation control section 201 and boiling section 203. For example, a wider interface opening may result in a shorter evaporation control section 201 and/or boiling section 203.

The application tip skin interface 205 is configured and manufactured to approximately cover only the target skin to be treated to both minimize the volume of liquified gas that is used on the patient's target skin, and also to minimize the cryosurgical effects on the patient's healthy skin (i.e., collateral tissue damage). Thus, the interface tip may be shaped to match the target skin. Different configurations for the interfaces are further shown in FIGS. 6A and 6B. In embodiments where the application tip skin interfaces 205 are separate from the evaporation control section 201 and the boiling section 203, the interfaces 205 are configured to mate with the boiling section 203 to enable single-handed use allowing for greater flexibility to the user.

Figure 6B:
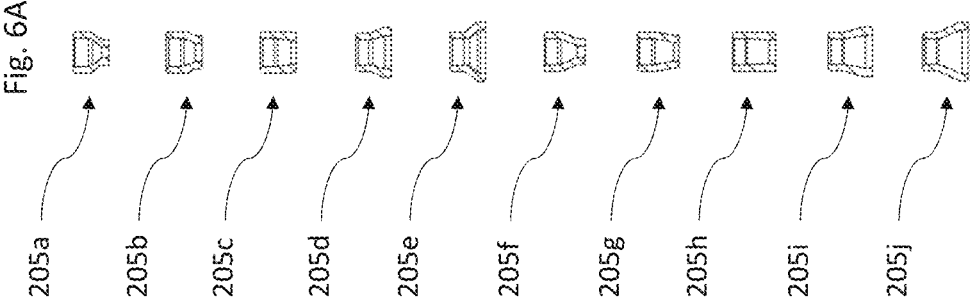
FIG. 6B shows a perspective view of an application tip skin interface in accordance with multiple embodiments of the invention.
Figure 6A:
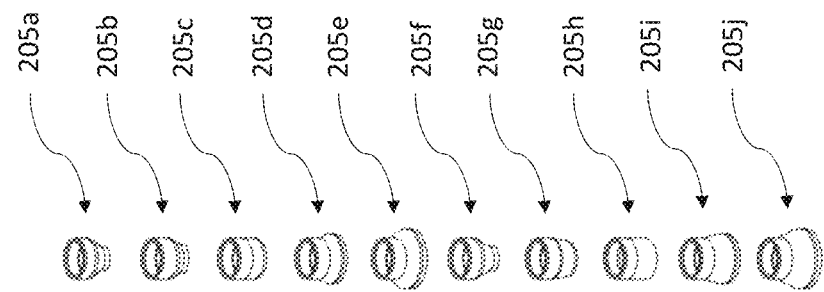
FIG. 6A shows a side view of an application tip skin interface in accordance with embodiments of the invention.

As shown in FIGS. 6A and 6B, in some embodiments of the invention, application tip skin interface 205 may be circular or ovular in shape, however, in other embodiments of the invention the skin interfaces 205 may include any number of geometric shapes including ovals, squares, rounded squares, rhombuses, diamonds, rounded diamonds, triangles, rounded triangles, and other geometrical shapes with or without rounded corners and/or edges. The skin interfaces 205 may also be adjusted to various non-normal geometric shapes (e.g., irregular shapes), for example, if the FTT device 101 is made from a malleable and/or moldable or cuttable material. As shown in embodiments 205a-205j in FIGS. 6A and 6B, the skin interfaces 205 may vary in size/shape. The skin interfaces 205 may vary in size, at least from 3-12 mm diameter (as shown in Table 1 below), however, may be configured to surround as much of the patient skin to be treated as possible.

Figure 7:
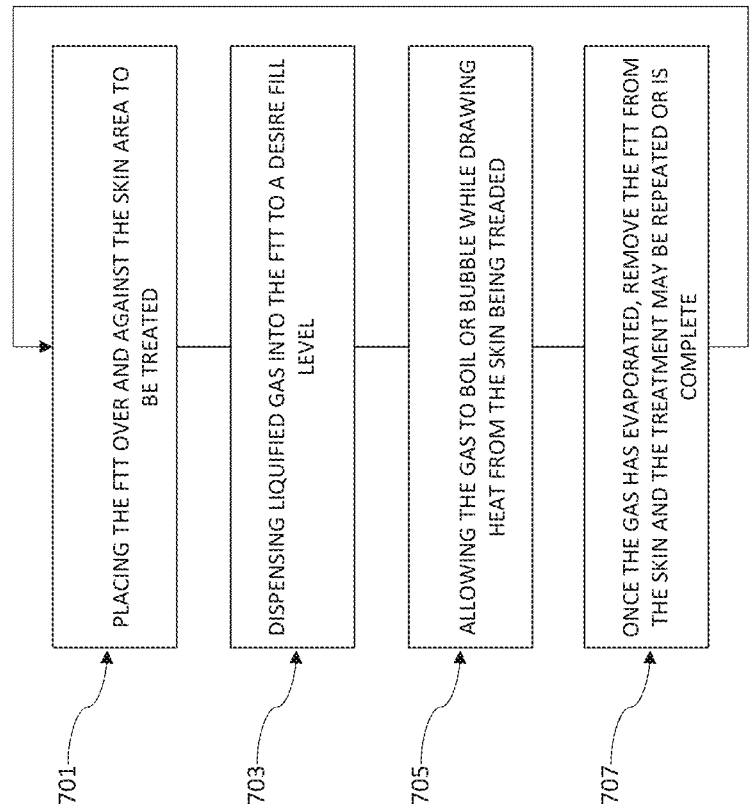
FIG. 7 describes a method of using an FTT device for cryosurgical applications in accordance with the invention.

A method of using the FTT device 101 with a cryosurgical system 100 is shown in blocks 701-707 of FIG. 7. As described in block 701, the FTT device 101, while mated to a dispensing device 103, is placed over and against the skin area to be treated with a liquified gas. The size and shape of the selected FTT device 101 is determined by approximating the size and shape of the area of the skin to be treated. This approximation limits damage to healthy skin. In block 703, the dispensing device 103 dispenses the liquified gas into the FTT device 101 to a desired fill level. Because the FTT device 101 is made of transparent or opaque materials, the user of the cryosurgical device 100 may be able to see the liquified gas in the FTT device 101. In block 705, the liquified gas is allowed to boil or bubble to draw heat from the treated skin. In block 707, the user watches the boiling/bubbling until it ends, i.e., the liquified gas has evaporated. The user may then remove the FTT device from the skin to determine whether the treatment was completed or if the treatment should be repeated. If repeated, the user may perform blocks 701-707 again to treat the affected skin.

FTT vs. Conventional Cone Comparison

Figure 5:
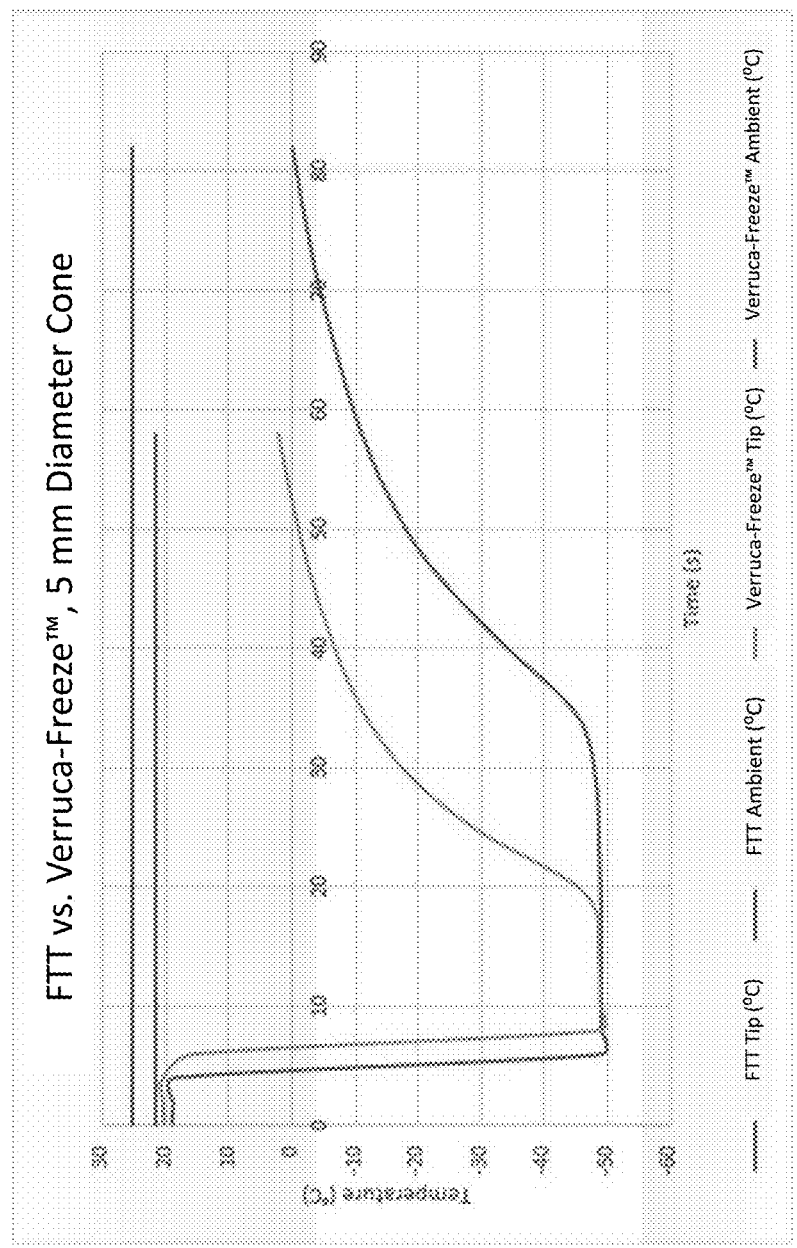
FIG. 5 is a graph of temperature variance over time of a liquified gas during a cryosurgical treatment in accordance with the invention.

In one experiment, approximately the same weight (0.7-0.8 g) of a gas mixture of pentafluoroethane (50%), difluoromethane (50%) was dispensed into the new invention FTT design and into a conventional product, Verruca-Freeze™, which uses a cone design originally disclosed in U.S. Pat. No. 5,200,170. Both the prior cone and the FTT device have a circular application area which is 5 mm in diameter. A thermocouple inserted beneath the orifice of the prior art cone and of the FTT was used to measure the temperature and time profile inside the bottom of each device to determine evaporation rates of the liquified gas in each device. As shown in FIG. 5, the FTT of the invention was able to hold its temperature substantially longer below −48° C., which is the measurable boiling point of the mixture of pentafluoroethane (50%), difluoromethane (50%) that was dispensed. The cone remained below −48° C. for 13±4 seconds, while the FTT of the invention remained below −48° C. for 25±6.7 seconds. Thus, the FTT device, in this example, was 100% more effective at controlling the rate of evaporation, which therefore increased the potential heat transferred from the target area.

In other experiments, the FTT devices and the Verruca-Freeze™ cones were filled again with approximately 1.3 g of the same liquified gas mix, and the time and temperature were measured until the liquified gas fully evaporated. The size of the interface to the skin was varied (i.e., the cross-sectional area of the skin interface 205 changed), and the surface to which the gas was applied (target treatment area) was varied.

As shown also in Table 1 below, the FTT device 101 more effectively slows the vaporization of the liquified gas. This effect was enhanced as the surface area of the treatment interface was increased while the mass of gas applied remained fixed. This increase in surface area at the interface corresponds with an increased influence from waste heat in the surrounding environment causing the gas in the cone to more quickly evaporate than gas in the FTT device 101. Thus, the FTT device lessens the amount of gas needed to increase potential heat transfer times resulting in an improved efficiency of the system.

TABLE 1

| Application Tip Skin Interface Diameter (mm) | FTT Average Time Below −48° C. (s) | Conventional Cone Average Time Below −48° C. (s) | % Difference |
|---|---|---|---|
| 3 | 99.6 | 76.6 | 23 |
| 5 | 72.8 | 58.2 | 21 |
| 9 | 49.6 | 41 | 18 |
| 12 | 32.4 | 17.6 | 44 |

The invention addresses design and ease of use difficulties of many previously available cryosurgical substance application systems. The invention provides an economical and easy to use platform when performing a large number of cryosurgical treatments.

The claimed invention is:

1. A focused treatment tip (FTT) device to interface with a cryosurgical device to control the rate of evaporation of liquified gas in contact with a patient, the device comprising:
   an evaporation control section, including a length and a cross-sectional area, wherein the evaporation control section receives the liquified gas from the cryosurgical device, and wherein the length and the cross-sectional area are selected based on the evaporation rate of the liquified gas;
   a boiling section in fluid communication with and between the evaporation control section and an application tip, the boiling section including a determined space for evaporation of the liquified gas while treating a targeted tissue treatment site of the patient, wherein the determined space for evaporation includes a volume selected based on the evaporation rate of the liquified gas; and
   an application tip to cover the targeted tissue treatment site of the patient and seal the FTT device to the targeted tissue treatment site of the patient,
   wherein the selected length and cross-sectional area of the evaporation control section and the volume of the boiling section are selected in combination to maintain the temperature of the liquified gas on the targeted tissue treatment site for a predetermined dwell time based on a boiling point of the liquified gas.

2. The FTT device of claim 1, wherein the FTT device includes a clear or translucent material to observe boiling of the liquified gas.

3. The FTT device of claim 1, wherein the FTT device includes at least one material selected from the group of a polymer, elastomer, metal, and silica.

4. The FTT device of claim 1, wherein the FTT device is contoured along its longitudinal axis with a flattening compound curve, and wherein the radii of the flattening compound curve are selected based on the evaporation rate of the liquified gas.

5. The FTT device of claim 1, wherein the liquified gas includes at least one liquified gas selected from the group of a hydrocarbon, fluorocarbon, hydrofluoro-olefin, and hydrofluorocarbon blend.

6. The FTT device of claim 5, wherein the at least one liquified gas includes at least one material selected from the group of propane, butane, dimethylether, 1,1,1,-trifluoroethane, pentafluoroethane, difluoromethanene, trifluoromethane, chlorodifluoromethane, 1,3,3,3-tetrafluoropropene, and nitrous oxide.

7. The FTT device of claim 1, wherein the application tip is sized and shaped to approximate the size and shape of the targeted tissue treatment site in an oval, square, rounded square, diamond, rounded diamond, triangle, or a rounded triangle.

8. A cryosurgical system, comprising:
   a liquified gas delivery device; and
   a focused treatment tip (FTT) device, comprising:
      an evaporation control section, including a length and a cross-sectional area, wherein the evaporation control section receives the liquified gas from the liquified gas delivery device, and wherein the length and the cross-sectional area are selected based on the evaporation rate of the liquified gas;
      a boiling section in fluid communication with and between the evaporation control section and an application tip, the boiling section including a determined space for evaporation of the liquified gas while treating a targeted tissue treatment site of a patient, wherein the determined space for evaporation includes a volume selected based on the evaporation rate of the liquified gas; and
      an application tip to cover the targeted tissue treatment site of the patient and seal the FTT device to the targeted tissue treatment site of the patient,
   wherein the selected length and cross-sectional area of the evaporation control section and the volume of the boiling section are selected in combination to maintain the temperature of the liquified gas on the targeted tissue treatment site for a predetermined dwell time based on the boiling point of the liquified gas.

9. The cryosurgical system of claim 8, wherein the FTT includes a clear or translucent material to observe boiling of the liquified gas.

10. The cryosurgical system of claim 8, wherein the FTT device includes at least one material selected from the group of a polymer, elastomer, metal, or silica.

11. The cryosurgical system of claim 7, wherein the FTT device is contoured along its longitudinal axis with a flattening compound curve, and wherein the radii of the flattening compound curve are selected based on the evaporation rate of the liquified gas.

12. The cryosurgical system of claim 8, wherein the liquified gas includes at least one liquified gas selected from the group of a hydrocarbon, fluorocarbon, hydrofluoro-olefin, and hydrofluorocarbon blend.

13. The cryosurgical system of claim 12, wherein the at least one liquified gas includes at least one material selected from the group of propane, butane, dimethylether, 1,1,1,- trifluoroethane, pentafluoroethane, difluoromethanene, trifluoromethane, chlorodifluoromethane, 1,3,3,3-tetrafluoropropene, and nitrous oxide.

14. The cryosurgical system of claim 8, wherein the application tip is sized and shaped to approximate the size and shape of the targeted tissue treatment site in an oval, square, rounded square, diamond, rounded diamond, triangle, or rounded triangle.

15. A method for treating a skin lesion using a cryosurgical device with a focused treatment tip (FTT) device, comprising:
  positioning the FTT device against a targeted tissue treatment site, wherein the FTT device comprises:
    an evaporation control section, including a length and a cross-sectional area, wherein the evaporation section receives the liquified gas and wherein the length and the cross-sectional area are selected based on the evaporation rate of the liquified gas;
    a boiling section in fluid communication with and between the evaporation control section and an application tip, the boiling section including a determined space for evaporation of the liquified gas while treating a targeted tissue treatment site, wherein the determined space for evaporation includes a volume selected based on the evaporation rate of the liquified gas; and
    an application tip to cover the targeted tissue treatment site and seal the FTT device to the targeted tissue treatment site, wherein the selected length and cross-sectional area of the evaporation control section and the volume of the boiling section are selected in combination to maintain the temperature of the liquified gas on the targeted tissue treatment site for a predetermined dwell time based on the boiling point of the liquified gas;
  receiving the liquified gas into the FTT device; and
  maintaining the FTT device against the targeted tissue treatment site for the predetermined dwell time while the liquified gas is evaporating.

16. The method of claim 13, further comprising:
  dispensing additional liquified gas into the FTT device and maintaining the FTT device against the targeted tissue treatment site when an additional application of the liquified gas is indicated.

\* \* \* \* \*